(12) United States Patent
Hurter et al.

(10) Patent No.: US 10,769,841 B2
(45) Date of Patent: Sep. 8, 2020

(54) SELECTIVE DISPLAY IN AN ENVIRONMENT DEFINED BY A DATA SET

(71) Applicant: ECOLE NATIONALE DE L'AVIATION CIVILE, Toulouse (FR)

(72) Inventors: Christophe Hurter, Toulouse (FR); Michael Traoré Sompagnimdi, Toulouse (FR)

(73) Assignee: ECOLE NATIONALE DE L'AVIATION CIVILE, Toulouse (FR)

( * ) Notice: Subject to any disclaimer, the term of this patent is extended or adjusted under 35 U.S.C. 154(b) by 0 days.

(21) Appl. No.: 15/979,778

(22) Filed: May 15, 2018

(65) Prior Publication Data
US 2018/0330532 A1    Nov. 15, 2018

(30) Foreign Application Priority Data

May 15, 2017  (EP) ..................................... 17305551

(51) Int. Cl.
| | |
|---|---|
| G06T 15/06 | (2011.01) |
| G06T 15/20 | (2011.01) |
| G06F 3/0481 | (2013.01) |
| G06T 11/20 | (2006.01) |
| G16H 40/63 | (2018.01) |

(Continued)

(52) U.S. Cl.
CPC ............ *G06T 15/06* (2013.01); *G06F 3/0481* (2013.01); *G06K 9/00771* (2013.01); *G06T 11/206* (2013.01); *G06T 15/10* (2013.01); *G06T 15/20* (2013.01); *G16H 30/40* (2018.01); *G16H 40/63* (2018.01); *G06K 2209/09* (2013.01); *G06T 2200/24* (2013.01)

(58) Field of Classification Search
None
See application file for complete search history.

(56) References Cited

U.S. PATENT DOCUMENTS

| | | | |
|---|---|---|---|
| 2002/0122038 A1 | 9/2002 | Cowperthwaite | |
| 2007/0116334 A1* | 5/2007 | Fidrich | .................... G06K 9/34 |
| | | | 382/128 |

(Continued)

FOREIGN PATENT DOCUMENTS

WO    2006099490 A1    9/2006

OTHER PUBLICATIONS

European Search Report for 17305551.8 dated Nov. 9, 2017.
(Continued)

*Primary Examiner* — Andrew G Yang
(74) *Attorney, Agent, or Firm* — Meagher Emanuel Laks Goldberg & Liao, LLP

(57) ABSTRACT

A mechanism is provided for exploring three dimensional environments such as those generated from X-ray and tomography scans, in such a way as to "see round" obstacles to an article of interest, without degrading the overall context of an article of interest in terms of it position in relationship to other articles, and to the viewpoint of the user. This is achieved by defining a light guide curve leading to the user's viewpoint, with respect to which ray tracing is performed to define the image displayed to the user whereby rays passing within a predetermined distance of the light guide curve at a relative angle within a predetermined range thereto are deviated so as to conform therewith to a degree proportional to its distance therefrom.

15 Claims, 9 Drawing Sheets

(51) Int. Cl.
*G06T 15/10* (2011.01)
*G16H 30/40* (2018.01)
*G06K 9/00* (2006.01)

(56) References Cited

U.S. PATENT DOCUMENTS

| | | | |
|---|---|---|---|
| 2011/0242097 A1 | 10/2011 | Miyamoto | |
| 2014/0240316 A1* | 8/2014 | Engle | G06T 15/06 345/426 |
| 2015/0042654 A1* | 2/2015 | Segasby | G06T 15/06 345/426 |
| 2016/0005209 A1* | 1/2016 | Dachsbacher | G06T 15/06 345/426 |
| 2016/0042559 A1* | 2/2016 | Seibert | G06T 15/506 345/426 |

OTHER PUBLICATIONS

Carpendale M S T: "A Framework for Elastic Presentation Space", Thesis Simon Fraser University, XX, XX, Mar. 1, 1999 (Mar. 1, 1999), pp. i-xi,1.

* cited by examiner

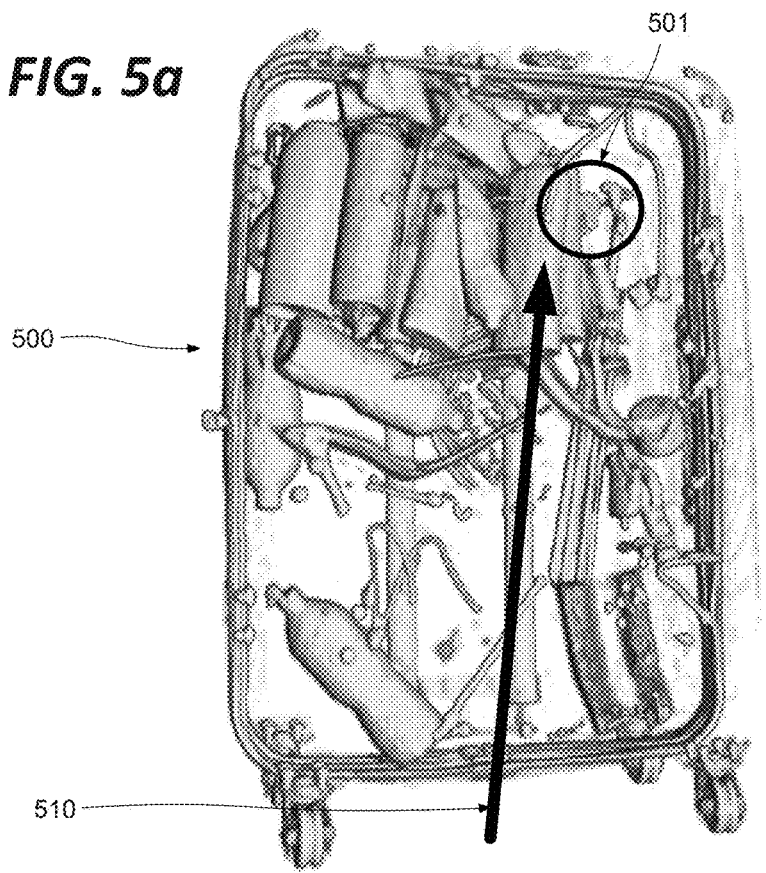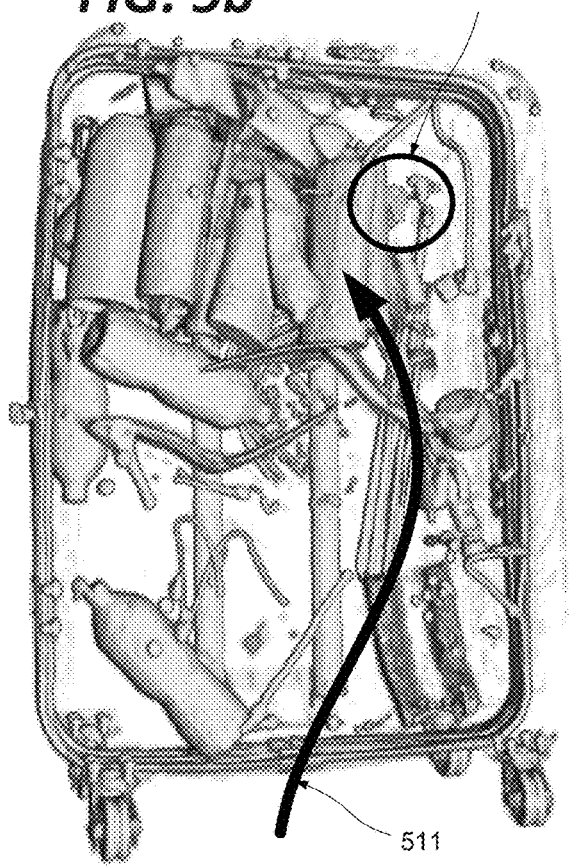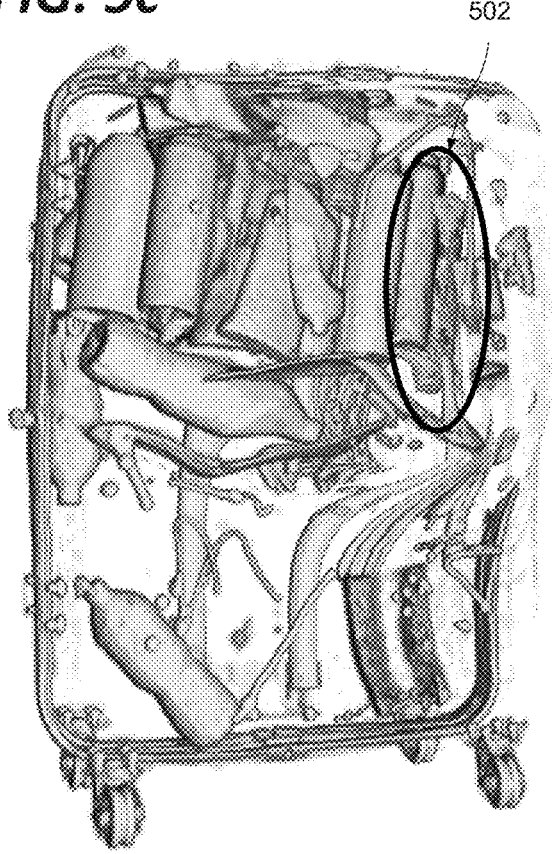

SELECTIVE DISPLAY IN AN ENVIRONMENT DEFINED BY A DATA SET

FIELD OF THE INVENTION

The present invention relates to the assisted exploration of virtual environments, and in particular to managing the difficulties associated with densely populated environments.

BACKGROUND OF THE INVENTION

Volumetric datasets are found in many fields, such as engineering, material sciences, medical imaging, astrophysics and more recently as volumetric virtual reality for entertainment. The exploration and manipulation of volumetric datasets is not trivial, often requiring extensive knowledge and is usually heavily impacted by the specific needs of users and is finding applications in a growing number of fields, for example in the medical and security professions as well as in the entertainment domain for games, virtual reality post production and user-based interaction. In the security domain, for example, in most airports security agents deal with such data exploration in the context of baggage inspections. Conventional X-ray imaging and tomography techniques based on imaging by sections or sectioning, through the use of any kind of penetrating wave, including x rays, acoustic waves, light (in thermo-acoustic tomography for example) an the like, are two commonly used fluoroscopic scanning systems. Conventional X-ray systems provide a flattened 2D scan while tomography systems produce transversal scans, also called slices. Thanks to data processing techniques such as the Radon transform, these systems can produce a full 3D scan, comprising a set of voxels with corresponding density data. Since the resulting X-ray scanned image only contains voxel or pixel densities, they cannot display the original material colours. The current standard colour visual mapping uses three different colours (orange, green, and blue) to display the data density. Orange colour corresponds to low density (mainly organic items). In opposition, blue colour is used for high density values (i.e. metal). In the case of X-ray systems, green colour corresponds to the superposition of different kinds of materials or average density materials. Images generated in this manner can be valuable in many fields, including for example luggage scanning, study of human body, combustion in motors, silicon chips, advanced materials, and so on.

FIG. 1 demonstrates, for the example of baggage inspection, some of the ways in which an article may be obscured in a scan. As shown in FIG. 1, the displayed 2D scanned image can suffer from four main issues:

Superposition:

A threat (e.g. prohibited object such as a bottle, a knife, cutter or the like) may be sheltered behind dense materials. Sometimes, it is possible "to see" through this blind shield using functionalities such as high penetration (enhanced X-ray power) or image processing (contrast improvement). As shown in FIG. 1, the umbrella and dense collection of objects in the upper right hand corner 101 may obscure articles of interest.

Location:

Depending on its location inside the luggage, a threat can be difficult to detect. Objects located in the corners, in the edges or inside the luggage's frame are very difficult to identify. As shown in FIG. 1, the retractable trolley bars and the rigid corners of the case 102 may obscure articles of interest.

Dissociation:

Another way to dissimulate a threat is to separate and to spread parts of it in the luggage (weapons or explosives are composed of many separated items like the trigger, the barrel . . . ). This dissociation can be combined with other dissimulation techniques. As shown in FIG. 1, a number of apparently non-descript items 103 are present which are unlikely to attract particular attention, but which may be assembled to form some article of interest.

Lure:

An ill-intentioned individual may use a lure to hide the real threat. For instance, a minor threat like a small pair of scissors may be clearly visible and catch a security agent's attention while a more important threat remains hidden. As shown in FIG. 1, the metal rod 104 may attract the attention of the user, drawing it away from some less visible threat.

Volumetric data exploration with direct volume rendering techniques is of great help to visually extract relevant structures in many fields of science: medical imaging, astrophysics and more recently in luggage security. To leverage this knowledge extraction, many techniques have been developed. A number of existing basic technologies are known in this field, including volume visualization, transfer function, direct voxel manipulation and focus plus context interaction.

In particular, volume visualization can be done with geometric rendering systems which transform the data into a set of polygons representing an iso-surface. The contour tree algorithm and other alternatives such as branch decomposition are usually used to find these iso-surfaces. Contour tree algorithms may be vulnerable to noise, which can be problematic for instance in luggage inspections since dense materials such as steel cause noise by reflecting the X-rays.

In order to investigate volumetric dataset, one can use the Transfer Function (TF). In practice, this maps the voxel density with a specific colour (including its transparency). Transfer functions can be 1, 2 or n dimensional and are of great help to isolate structures of interest in volumetric data. Thanks to the colour blending process, a suitable transfer function can also reveal iso-surfaces or hide density to improve the volumetric data visualization.

FIG. 2 illustrates a difficulty arising in the context of FIG. 1.

A specific difficulty that arises in an environment such as that described with respect to FIG. 1 is that the user's view, which may be defined for example as shown in terms of a virtual viewpoint 200 having a specified position, axis of orientation 201 and field of view θ 202, of a particular article or region of interest such as the article 210 will often be obscured by materials of less or no interest such as the article 220. In order to better view the object or region of interest, the user may wish disregard certain such materials so as to achieve an improved view.

There is thus a need of mechanisms supporting the generation of such improved views.

SUMMARY OF THE INVENTION

In accordance with a first aspect of the invention, there is provided an apparatus for processing objects having a spatial relationship in a three dimensional environment defined by a data set for display. The apparatus comprises:

a virtual viewpoint selection interface adapted to define a viewpoint in the environment having a specified position, axis of orientation and field of view therein, a light guide curve selection interface adapted to define a light guide curve which the axis converges with at the virtual viewpoint, a ray tracer adapted to simulate the projection of a plurality of light rays within the environment from the viewpoint, the rays all having an incident angle to the viewpoint within the field of view, and to deviate each ray so as to conform with the light guide curve to a degree proportional to its distance therefrom, a display frame compiler adapted to compile an image composed from the elements of said environment struck by the rays.

In a development of the first aspect, the light guide curve selection interface comprises a human interface device.

In accordance with the present invention, in a second aspect, there is provided a method of displaying objects having a spatial relationship in a three dimensional environment defined by a data set, the method comprising the steps of:

defining a virtual viewpoint in the environment having a specified position, axis of orientation and field of view therein, defining a light guide curve which converges with the axis at said virtual viewpoint, projecting a plurality of simulated light rays within the environment from the viewpoint, the rays all having an incident angle to the viewpoint within the field of view, and deviating each ray so as to conform with the light guide curve to a degree proportional to its distance therefrom, and compiling an image composed from the elements of said environment struck by the rays.

In a development of the second aspect, the light guide curve is defined as one or more polynomial curves.

In a development of the second aspect, the step of defining a light guide curve comprises defining an initial light guide curve having a knot or control point under user control, and the step of defining a light guide curve further comprises receiving user input defining a position of the knot or control point and modifying the initial light guide curve to obtain the light guide curve.

In a further development of the second aspect, the method comprises the further step of receiving user input defining the light guide curve.

In a further development of the second aspect, the step of receiving user input defining the light guide curve comprises receiving a manually traced line via a user interface device, the manually traced line representing said light guide curve.

In a further development of the second aspect, the method comprises the further step of translating the manually traced line into one or more polynomial curves in the three dimensional environment.

In a further development of the second aspect, the light guide curve is defined by applying a routing algorithm so as to define a path to a first point in the environment whilst contouring a second point in the environment, where the first point and the second point are designated by user input.

In a further development of the second aspect, the guide curve and the proportional relationship according to which any said ray passing within a predetermined distance of the light guide curve at a relative angle within a predetermined range thereto is deviated, together simulate the effect of the optical deformation of a physical lens on the rays.

In a further development of the second aspect, the transformation comprises reducing luminous intensity of each ray contributing to the displayed image the further it is from the light guide curve.

In a further development of the second aspect, the objects are voxels, polygons, or the objects are defined by intersecting surfaces.

In a further development of the second aspect, the method comprises the further step of receiving an external input determining the orientation, position or field of view of said viewpoint.

In accordance with the present invention in a third aspect, there is provided a computer program adapted to implement the steps of the second aspect.

In accordance with the present invention in a fourth aspect, there is provided a computer readable medium incorporating the computer program of the third aspect.

BRIEF DESCRIPTION OF THE DRAWINGS

The above and other advantages of the present invention will now be described with reference to the accompanying drawings, presented for illustration purposes, in which:

FIGS. 5a-c show the application of an embodiment to a real image, in particular:

FIG. 5a shows a section of a suitcase 501 similar to that described with respect to FIG. 1 in a first view, FIG. 5b shows the section of a suitcase 501 corresponding to that of FIG. 5a, and FIG. 5c shows an alternative view 502 of the suitcase shown in FIGS. 5a and 5b;

DETAILED DESCRIPTION

Figure 2:
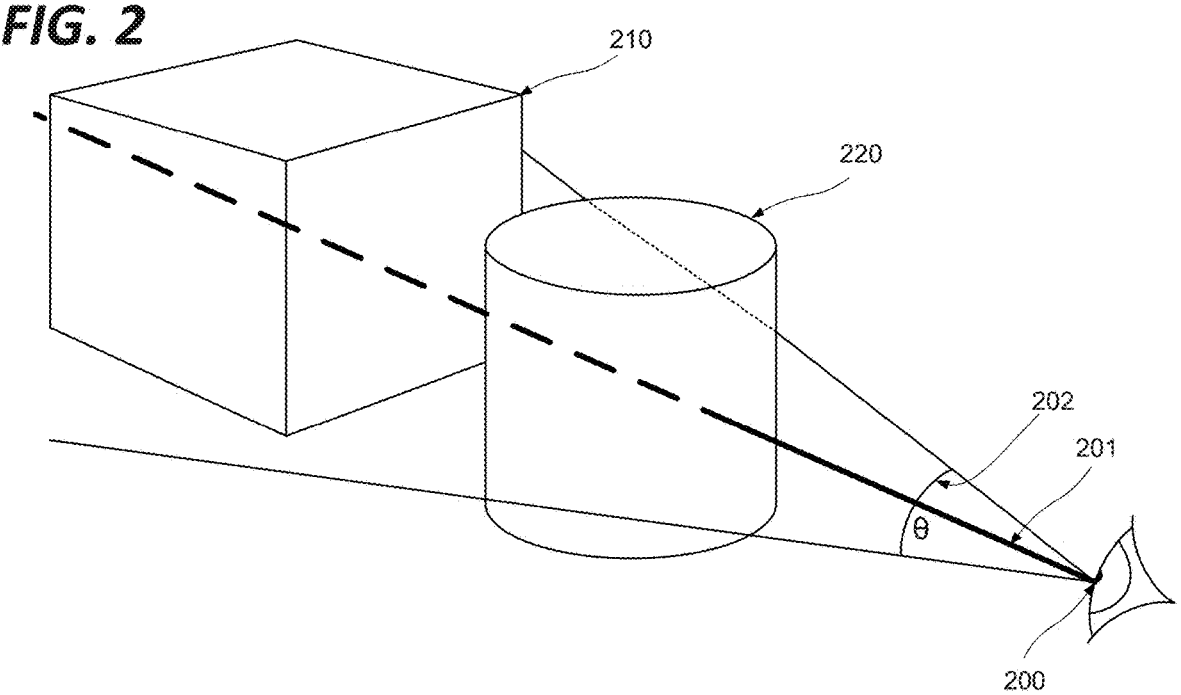
FIG. 2 illustrates a difficulty arising in the context of FIG. 1.

As discussed with respect to FIG. 2 above, when displaying objects having a spatial relationship in a three dimensional environment, which may be computer generated, the user may wish to disregard certain of such objects or parts thereof so as to achieve an improved view of an object or area of interest. While prior art approaches may provide methods for selectively removing objects from the environment on a temporary basis to remove the obstruction, this approach inherently undermines the context of the object of interest, which will often be important to properly interpreting the representation. With known solutions, there is also a risk of removing material which is itself of possible interest, although the user may not yet realise the significance thereof. Another alternative approach to this problem is simply to change the viewpoint, however in densely occupied environments, it may often prove impossible to find any point of view with a clear view of the point in question.

Figure 3:
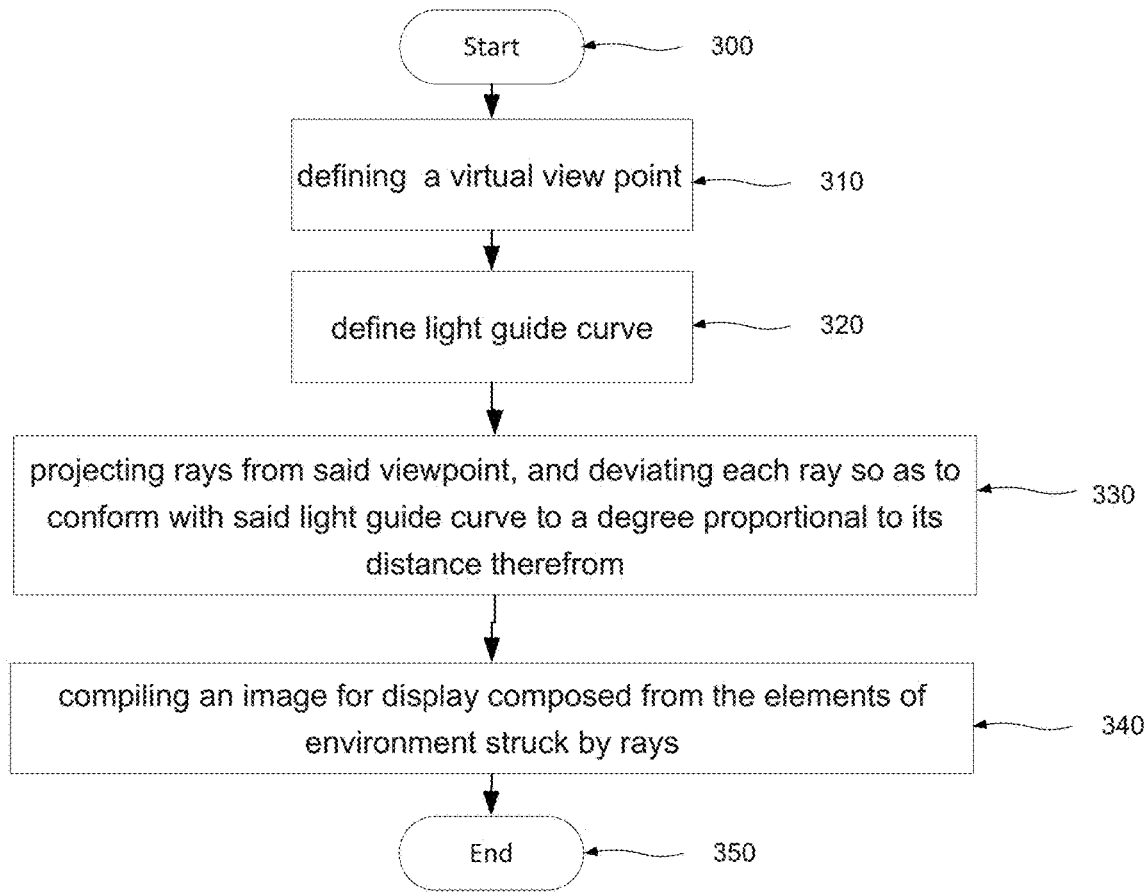
FIG. 3 shows a method in accordance with an embodiment.

FIG. 3 shows a method in accordance with an embodiment. In particular, FIG. 3 shows steps of a method of displaying objects having a predefined spatial relationship in a three dimensional environment.

The three dimensional environment may be defined in any suitable terms, such as for example voxels, polygons (for example in polygon mesh structures), intersecting surfaces (for example NURBS surfaces or subdivision surfaces) or equation-based representations. As such, the environment may comprise objects defined in terms of voxels, polygons, or intersecting surfaces.

In such an environment, the objects may be associated with a respective metadata value, which can be used to define the respective visibility of said objects in representations thereof. This value may directly define the opacity of the object when displayed, or some other visibility value such as brightness or colour, or may reflect a physical characteristic of the real substance represented by the object. For example, where the objects represent components of physical artefacts such as described with respect to FIG. 1, i.e. in the context of a scan representing those artefacts, the metadata value may represent the density of the material in question, which may then be translated into opacity, brightness, etc. when the objects are displayed.

As shown in FIG. 3, the method begins at step 300 before proceeding to step 310, at which a virtual viewpoint such as viewpoint 200 as introduced above is defined in the environment, in terms of a specified position, axis of orientation and field of view in that environment.

In certain embodiments, the orientation, position or field of view of the viewpoint may be defined on the basis of external input, for example via a user interface as discussed in more detail hereafter, so that a user can explore the environment by shifting the viewpoint.

The position of the viewpoint may be any position in the environment. In some cases, it may be desirable to exclude positions falling within other objects defined in the environment.

The orientation of the viewpoint may be any combination of altitude and azimuth values.

The field of view of the viewpoint may be any angular value. In many embodiments, it will be less than 180 degrees. In some cases it may be desirable for the angle to approach that of human vision, usually between 70 and 20 degrees. In some cases, for example where it is intended that an image derived from the point of view be presented on a non-circular display, the field of view may vary depending on the angle of the edge of the field of view with respect to the plane perpendicular to the axis of orientation.

The method next proceeds to the step 320 of defining a light guide curve which converges with the axis at the virtual viewpoint.

Figure 4:
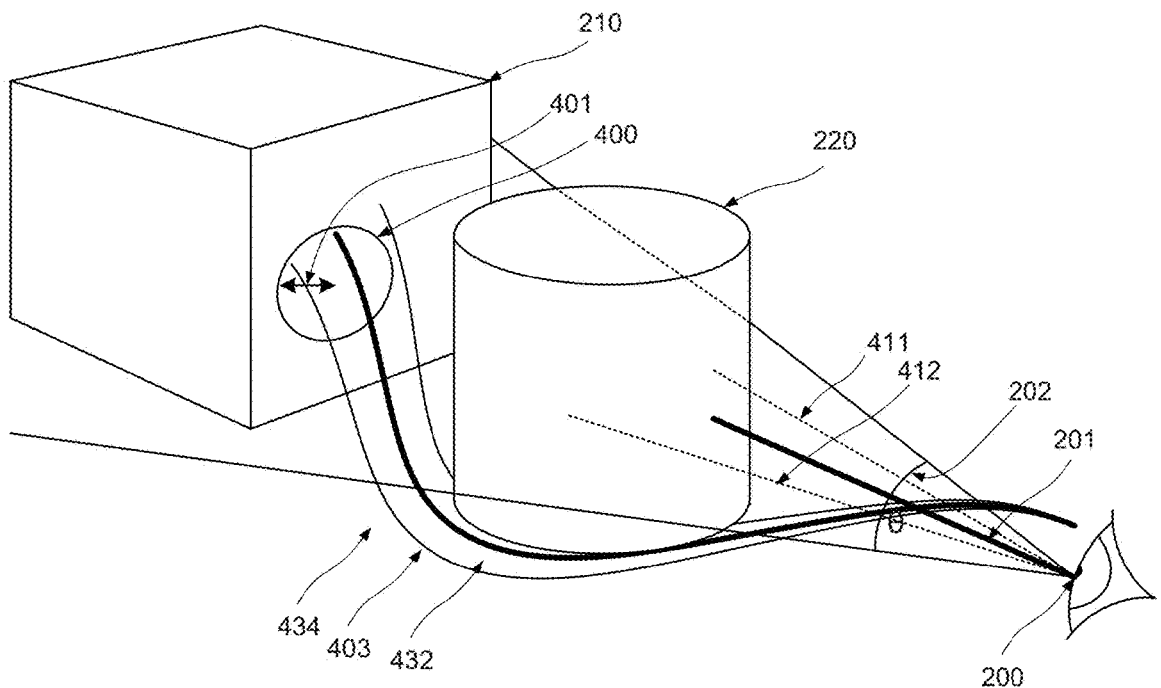
FIG. 4 presents an exemplary environment illustrating embodiments.

FIG. 4 presents an exemplary environment illustrating some embodiments. FIG. 4 includes the objects 210 and 220, and the viewpoint 200 as described with reference to FIG. 2. Furthermore as shown, there is provided a light guide curve 403. As shown, this curve describes a path from the viewpoint 200 to the surface of the object 210, via an indirect, curving path which passes around the object 220.

The light guide curve may be defined as one or more polynomial curves, such as a spline. The light guide curve may be defined as a sequence of straight lines. The light guide curve may be defined in a single plane, or may be three-dimensional.

The light guide curve may be manually traced by a user using a mouse, touch sensitive display or other two-dimensional interface device. The light guide curve may be manually traced by a user using a game controller, stylus, wand, gesture, mobile phone or other device that may be used to trace a path in three-dimensional space. This approach may be combined with a projection of the environment in three dimensions using holographic projections such as Microsoft® Hololens or Metavision™ systems, 3d goggles such as Google® Glass or the like. The light guide curve may be defined by recording a path through the environment as directed via a user interface, for example using conventional three-dimensional navigation controls. The light guide curve may be defined by applying a routing algorithm so as to define a path to a first point in said environment whilst contouring a second point in the environment, where said first point and said second point are designated by user input. This routing may be performed by way of example by means of a meta-heuristic algorithm such as Simulated Annealing to find a suitable path between the position of the virtual viewpoint and a designated target area. In certain embodiments, any number of obstacles may be contoured to as to automatically define a path presenting the minimal possible degree of obstruction between a virtual viewpoint and a designated target area. This approach may be extended to any arbitrary number of points to be contoured. The same approach may also be applied to objects defined in the environment in the place of points, or objects may be converted into sets of points. Points or objects may be selected by the user using standard user interface operations such as clicking on particular locations to select points or objects to be contoured.

For the light guide curve to provide distortions that are intuitively understandable to the user, it may be desirable to ensure that the light guide respects certain realism requirements. For example, it may be required that the line is continuous, that is does not intersect with itself, that it does not describe excessively tight turns or sharp angles, and the like. This may be treated as an optimization problem, whereby the light guide curve may be modelled as the path of a moving object with a given maximum speed and a maximum curvature. The method of FIG. 3 next proceeds to step 330 at which a plurality of simulated light rays 411, 412 are projected within the environment from the viewpoint 200 having an incident angle to the viewpoint within said field of view θ, and deviating each ray so as to conform with said light guide curve 403 to a degree proportional to its distance therefrom. Thus as shown the rays 411, 412 are deviated to conform to the light guide curve to form deviated rays 432, 434.

This proportional relationship need not be linear, but includes any effect where the degree of deviation is determined taking into account the distance from the light guide curve.

Still further, the effect may be applied up to a predetermined distance of the light guide curve, and not outside that predetermined distance, so that a discontinuity is defined between the image modified with reference to the light guide curve, and the rest of the image projected in the conventional manner. Where this approach is adopted, an intermediate zone between the image modified with reference to the light guide curve, and the rest of the image projected in the conventional manner may be generated to soften this discontinuity, for example by interpolating or "morphing" between the outer pixels of the image modified with reference to the light guide curve, and corresponding inner pixels of the rest of the image projected in the conventional manner.

Still further, the degree to which rays are deviated towards the light guide curve may vary along the length of the light guide curve. In particular, the degree of deviation may be increased to whatever degree is necessary for a set of rays corresponding to a particular final view to pass through a narrow gap occurring at a point between the viewpoint and the designated target area, thereby avoiding occlusion from the object defining the gap.

Still further, the degree of deviation may be set to an arbitrary value in a target zone close to the designated target area, so as to define the final field of view of the image presented to the user. In particular, the rays may be set to deviate strongly in the target zone so as to provide a wide angle, extreme wide angle or fish-eye type field of view of the vicinity of the designated target area to the user. Alternatively the rays may be set to converge in the target zone so as to advantageously provide a microscopic type field of view of the vicinity of the designated target area to the user.

The method next proceeds to step 340 at which an image is compiled for display composed from the elements of said environment struck by said rays. This image may then be presented to a user.

As such, the resulting image will advantageously provide a point of view which provides a complete, unexpurgated view of the environment, whilst reducing or removing obstructions.

In accordance with certain embodiments, the shape of the guide curve and the definition of the proportional relationship according to which any ray passing within a predetermined distance of the light guide curve at a relative angle within a predetermined range thereto, together simulate the effect of the optical deformation of a physical lens on said rays. For example, the effect may simulate barrel distortion. This effect may advantageously render interpretation of the resulting image more intuitive to a user.

In accordance with certain embodiments, the luminous intensity of each ray contributing to the displayed image is reduced to a degree proportional to the distance it is from said light guide curve. As such, the optical effect known as "vignetting" may be simulated. This effect may advantageously render interpretation of the resulting image more intuitive to a user.

The light guide curve may be emitted from the centre of the field of view, or depart at any angle from the viewpoint. This advantageously permits the possibility of moving the area of distortion within the field of view.

In some embodiments, the light guide curve may be defined by a representation of the curve input by a user, for example by means of a user interface. For example, the user may trace the light guide curve with a finger, stylus, mouse pointer or other cursor control device. As appropriate, additional processing may be applied to smooth or otherwise optimise the input line to constitute the light guide curve in view of system requirements.

FIGS. 5*a-c* show the application of an embodiment to a real image.

Figure 1:
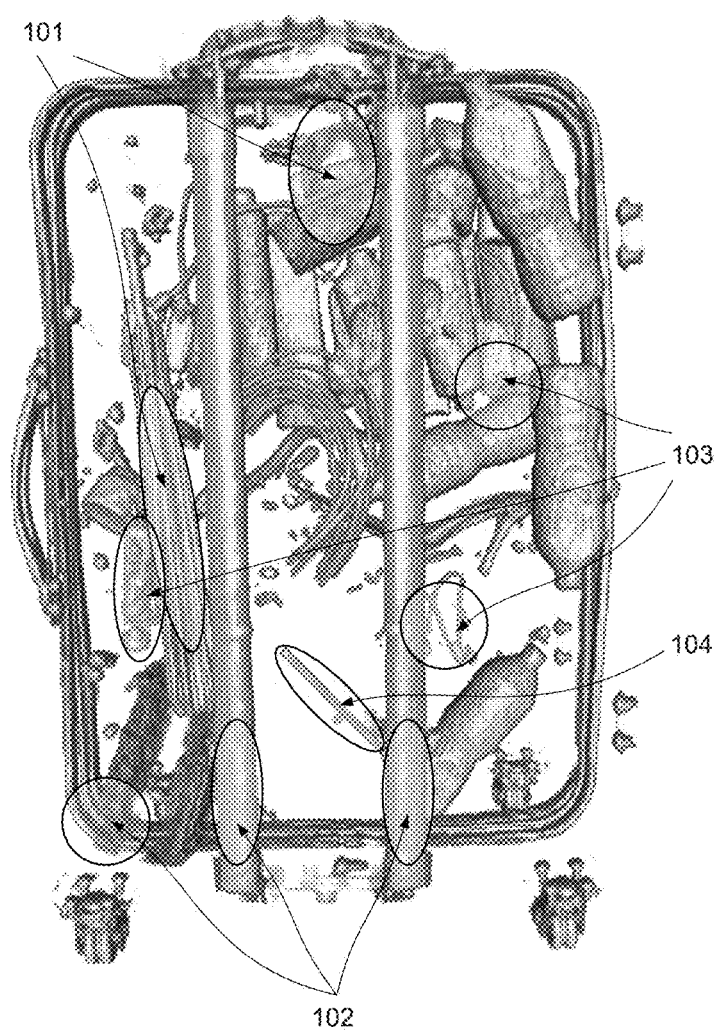
FIG. 1 presented above, demonstrates some of the ways in which an article may be obscured in a scan.

FIG. 5*a* shows a section of a suitcase 500 similar to that described with respect to FIG. 1 in a first view. The arrow 510 represents schematically the angle of view with respect to which the displayed image is generated, the light guide curve in this case being a straight line as may be found in conventional tools for navigating a three-dimensional environment. Although at first sight the suitcase 500 does not contain any suspicious articles, a viewer's interest may be aroused by the key shaped surface 501.

FIG. 5*b* shows the section of a suitcase 500 corresponding to that of FIG. 5*a*. In this case, the viewer's interest has been aroused by the key shaped surface 501, and the viewer has manipulated the light guide curve as shown schematically by the line 511. As shown, the light guide curve 511 has been manipulated to describe a curve sweeping round to the right before swinging back in to the heart of the suitcase, in such a way as to partially skirt the articles obscuring the view of the suspicious article 501.

FIG. 5*c* shows an alternative view 500 of the suitcase shown in FIGS. 5*a* and 5*b*. In this case the view of the suitcase 500 corresponds to a view obtained by deviating rays passing near the modified light guide curve 511 as shown in FIG. 5*b* so as to present a modified view in which the part of the displayed image corresponding to the vicinity of the object of interest is distorted with respect to the surrounding parts of the suitcase so as to provide an alternative, less obstructed view of the object of interest 502. As can be seen in FIG. 5*c*, as an important result, with the benefit of this clearer view, it is apparent that the article 502 is in fact a pistol. As mentioned above, the proportional relationship between the degree of distortion applied to rays and their distance from the light guide curve needs not be linear, but includes any effect where the degree of deviation is determined taking into account the distance from the light guide curve. As shown in FIG. 5*b*, the proportional relationship obeys an exponential decay law, such that a relatively constant degree of deviation is applied in a region close to the light guide curve, which then rapidly falls away in a region showing visible distortion, before approaching zero for the remainder of the image, which accordingly corresponds closely to the original, undistorted image as shown for example in FIGS. 5*a* and 5*b*. The relationship may be linear, polynomial, or more complex, including any arbitrary transfer function. In particular, the relationship may define zero deviation outside a particular angular field.

As mentioned above, this proportional relationship may be defined so as to imitate the defects of an optical lens, for example presenting barrel, pin cushion or other distortion effects, or other effects such as flare, bokeh or vignetting.

In any embodiment, the field of view, orientation, or position of the viewpoint, the light guide curve geometry or the proportional relationship may be dynamically selected by user input. The proportional relationship may be directly defined by a user tracing a transfer function defining the relationship, for example in terms of distortion effect as a function of distance along the line from the viewpoint.

The user may thus adjust the light guide curve defining the manner in which the displayed image is compiled, to view items of interest from alternative viewpoints, without the coherence set of objects comprising the suitcase contents, and the relative position of any article of interest being compromised. By this means, the user retains a strong intuitive understanding of the interrelationship between the objects in the suitcase, and their relative contexts. In this particular case, the virtual projector (not shown) is fixed in a plane at the same distance from the suitcase as the virtual camera, and with the same orientation as the virtual camera, but may be moved by the user or automatically around that plane to render visible different zones in the virtual camera's field of view. The user may also select different display functions, and in particular vary the distance scaling term so as to display deeper or shallower parts of the suitcase.

Figure 6:
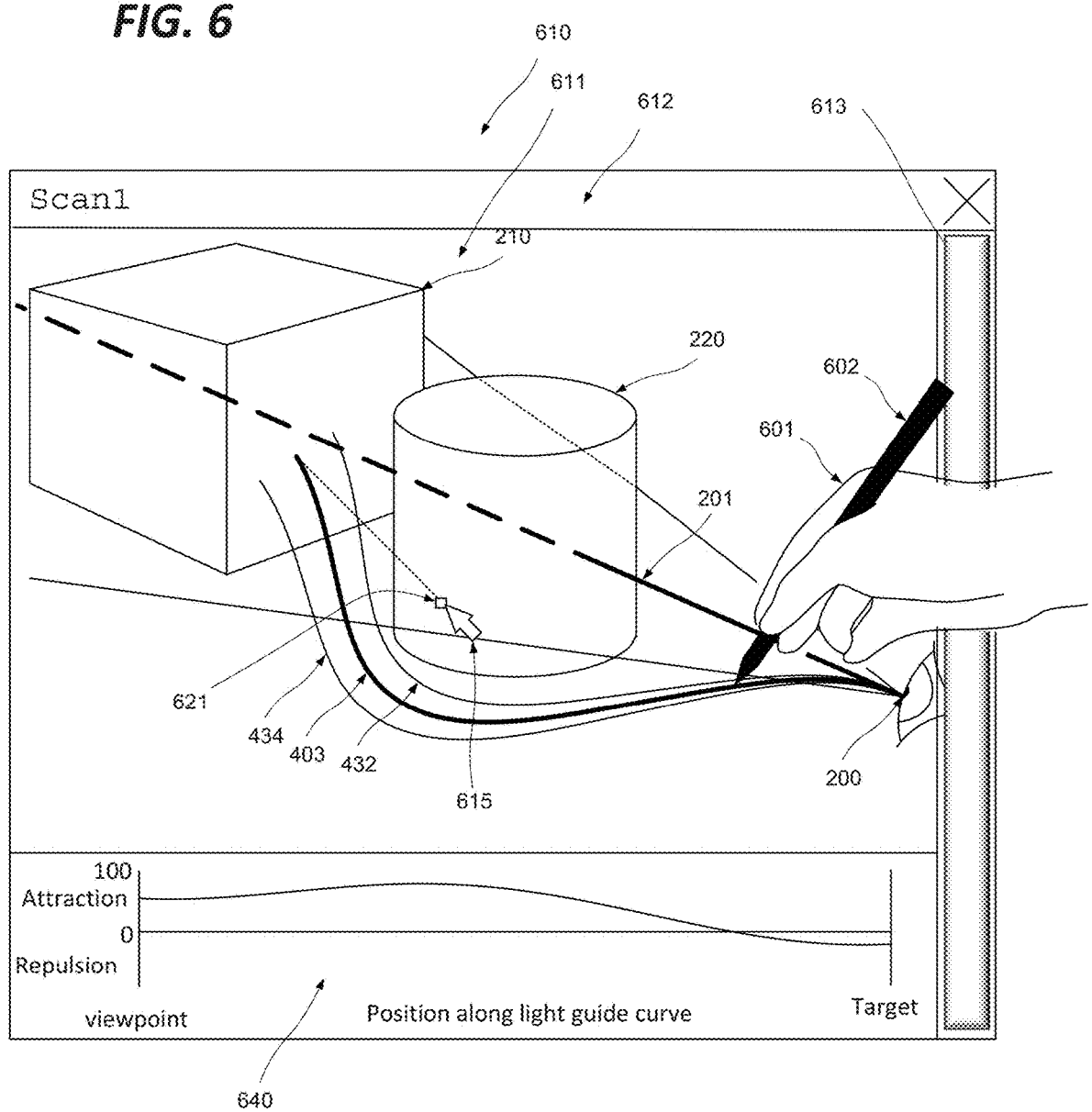
FIG. 6 shows a representation of a graphical representation environment in accordance with an embodiment.

FIG. 6 shows a representation of a graphical representation environment in accordance with an embodiment. In this embodiment, the environment is shown by way of example in a typical generic graphical user interface. Specifically, as shown in FIG. 6, there is provided a window 610 in a graphical user interface. As shown the window 610 comprises an editing pane 611, title bar 612, slider bar 613 and pointer 615 as examples of typical GUI interface features.

The editing pane 611 displays a graphical representation of objects 210 and 220 as described above by way of example.

Furthermore, FIG. 6 illustrates the definition of a path 403 in accordance with certain embodiments. As shown, a user's hand 601 is using a stylus 602 to describe the path 403, which skirts object 220 as described above, for example by means of a touch screen interface, mouse, trackerball, light pen or the like. This freehand curve may be converted into a spline or other compact representation, and translated into a three-dimensional path in the three-dimensional environment in which the objects 210 and 220 are defined. This translation may be performed by means of mathematical tools such as spline decomposition or functional decomposition, or any other technique for turning a series of discrete points into a continuous line. Alternatively, the user may directly manipulate such a spline function representing the modified light guide curve, for example by dragging control points or knots defining the curve. For example, the cursor 615 may be used to drag a control point such as the control point 621. Similarly, a control point may be fixed to a specific point in the user's field of view, so that when the user's point of view is changed in a conventional manner by tilt, pan, dolly or truck movements of the virtual camera defining the viewpoint, a control point of the light guide curve is moved in the three-dimensional environment to remain in the same position in the user's field of view as that field of view shifts, or alternatively to remain fixed in the same position in the three-dimensional environment as the field of view is changed.

It will be appreciated that while the mechanism of FIG. 6 is described with reference to a manually controlled interface such as a touch screen interface, mouse, trackerball, light pen or the like, any other human interface mechanism may be used to enable the user to define the light guide curve. In particular, the light guide curve may be defined by tracking the movement of any part of the user's body, such as the users head, or the focus of the user's gaze (eye tracking). Speech and/or voice recognition; and electric-field sensing componentry for assessing brain activity may equally be used. Any or all of these techniques may be used together to provide a convenient and effective input interface. Such interface mechanisms may equally be used for the definition of the position, orientation and field of view of the viewpoint. In certain such embodiments, the user might selects the location of the viewpoint then define the orientation of the viewpoint with reference to the user's head orientation.

FIG. 6 further shows a transfer function window 640. The transfer function window as shown presents a transfer function defining the variation in the distortive effect of the light guide curve on nearby rays along its length. As shown, the transfer function defines a distortion effect whereby rays are attracted to the line along most of its length, compressing the ray bundle so as to pass between obstacles, before switching to a repulsive effect, achieving a wide angle view close to the target. The user may be able to select predefined transfer functions from a list, and/or manually define the transfer function by dragging control points of the transfer function curve, using a cursor or otherwise.

The disclosed methods can take form of an entirely hardware embodiment (e.g. FPGA), an entirely software embodiment (for example to control a system according to the invention) or an embodiment containing both hardware and software elements. As such, embodiments may comprise a number of subsystems, functional elements or means adapted to implement the invention in communication with each other, and/or with standard fixed functions or programmable elements for example as described below.

Figure 7:
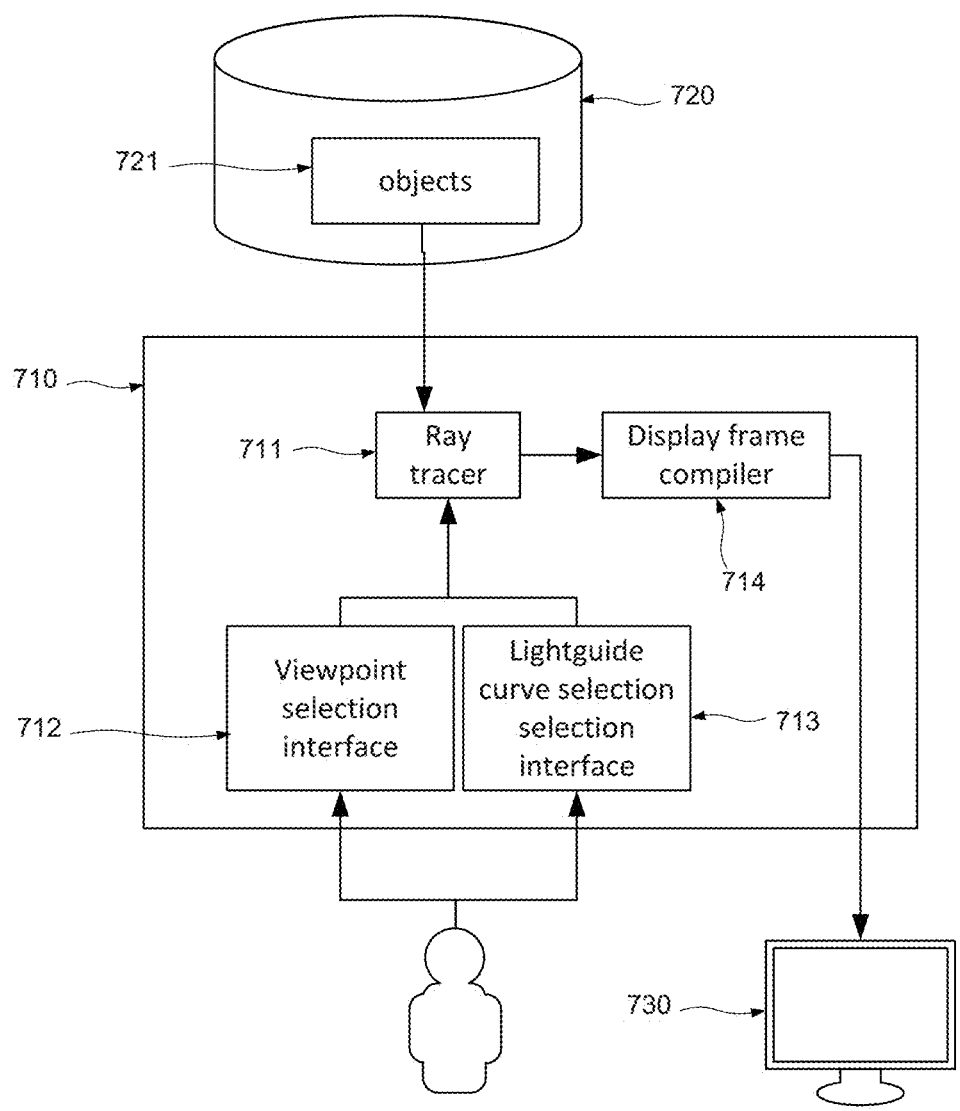
FIG. 7 shows an apparatus in accordance with an embodiment.

FIG. 7 shows an apparatus in accordance with an embodiment.

In particular, there may be provided an apparatus 710 for processing objects 721 having a predefined spatial relationship in a three-dimensional environment (represented by way of example as a database 720) for display. As shown, the apparatus 710 comprises a virtual viewpoint selection interface 712 adapted to define a viewpoint in the environment 720 having a specified position, axis of orientation and field of view therein, and a light guide curve selection interface 713 adapted to define a light guide curve with which the axis converges at the virtual viewpoint. More particularly, the light guide curve may be tangential to the axis at the virtual viewpoint. The light guide curve selection interface may be adapted to support any of the methods of light guide curve definition discussed above, including automatic and manual definition, or combination of both. Where the definition methodology includes automated aspects, the light guide curve may incorporate hardware or software components adapted to perform those functions. Where the definition methodology calls for manual input, the light guide curve selection interface may communicate with input devices for example as discussed in more detail hereafter to receive and interpret the user input in the context of light guide curve definition.

The light guide curve selection interface and/or the virtual viewpoint selection interface may comprise a human interface device such as a mouse, touchscreen, eye tracker, stylus or any other mechanism for receiving a user definition of a line as discussed herein or otherwise, for example as discussed further hereafter.

The apparatus 710 further comprises a ray tracer 711 adapted to simulate the projection of light rays within said environment from one or more virtual light sources, and to deviate any ray passing within a predetermined distance of the light guide curve at a relative angle within a predetermined range thereto so as to conform therewith to a degree proportional to its distance therefrom, and a display frame compiler 714 adapted to compile an image for display composed from the rays arriving at said virtual viewpoint at an incident angle within said field of view. As shown, and by way of example only, the display frame compiler 714 outputs data to a display unit 730, although this might equally be virtual reality headset, specific glasses, printer, 3D printer, projector or any other means of visually rendering the image.

In certain embodiments, including those where the light guide curve is defined automatically, the light guide curve may evolve progressively from a straight line in a conventional display to the final light guide curve by way of a number of intermediate steps, with the image for display being recomposed at each step, so that the user sees a progressive evolution in viewpoint. The number of steps may be sufficient to ensure an illusion of a smooth transition. The rate of this transition may be varied or even paused under the control of the user. The user may additionally intervene to adjust parameters such as the destination point, sensitivity to obstructions and the like, so as to change the light guide curve as it is generated.

On this basis, there is provided a mechanism for exploring three-dimensional data sets representing real or environments such as those generated from X-ray and tomography scans, in such a way as to "see round" obstacles to an article of interest, without degrading the overall context of an article of interest in terms of its position in relationship to other articles, and to the viewpoint of the user. This is achieved by defining a light guide curve leading to the user's viewpoint, with respect to which ray tracing is performed to define the image displayed to the user whereby rays passing within a predetermined distance of the light guide curve at a relative angle within a predetermined range thereto are deviated so as to conform therewith to a degree proportional to its distance therefrom.

Similarly, there is provided an apparatus adapted to perform the steps of any of the methods described above, for example with respect to FIG. 3.

Software embodiments include but are not limited to applications, firmware, resident software, microcode, etc. The invention can take the form of a computer program product accessible from a computer-usable or computer-readable medium providing program code for use by or in connection with a computer or an instruction execution system.

A computer-usable or computer-readable can be any apparatus that can contain, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium.

In some embodiments, the methods and processes described herein may be implemented in whole or part by a user device. These methods and processes may be implemented by computer-application programs or services, application-programming interface (API), a library, and/or other computer-program product, or any combination of such entities.

The user device may be a mobile device such as a smart phone or tablet, a drone, a computer or any other device with processing capability, such as a robot or other connected device.

Figure 8:
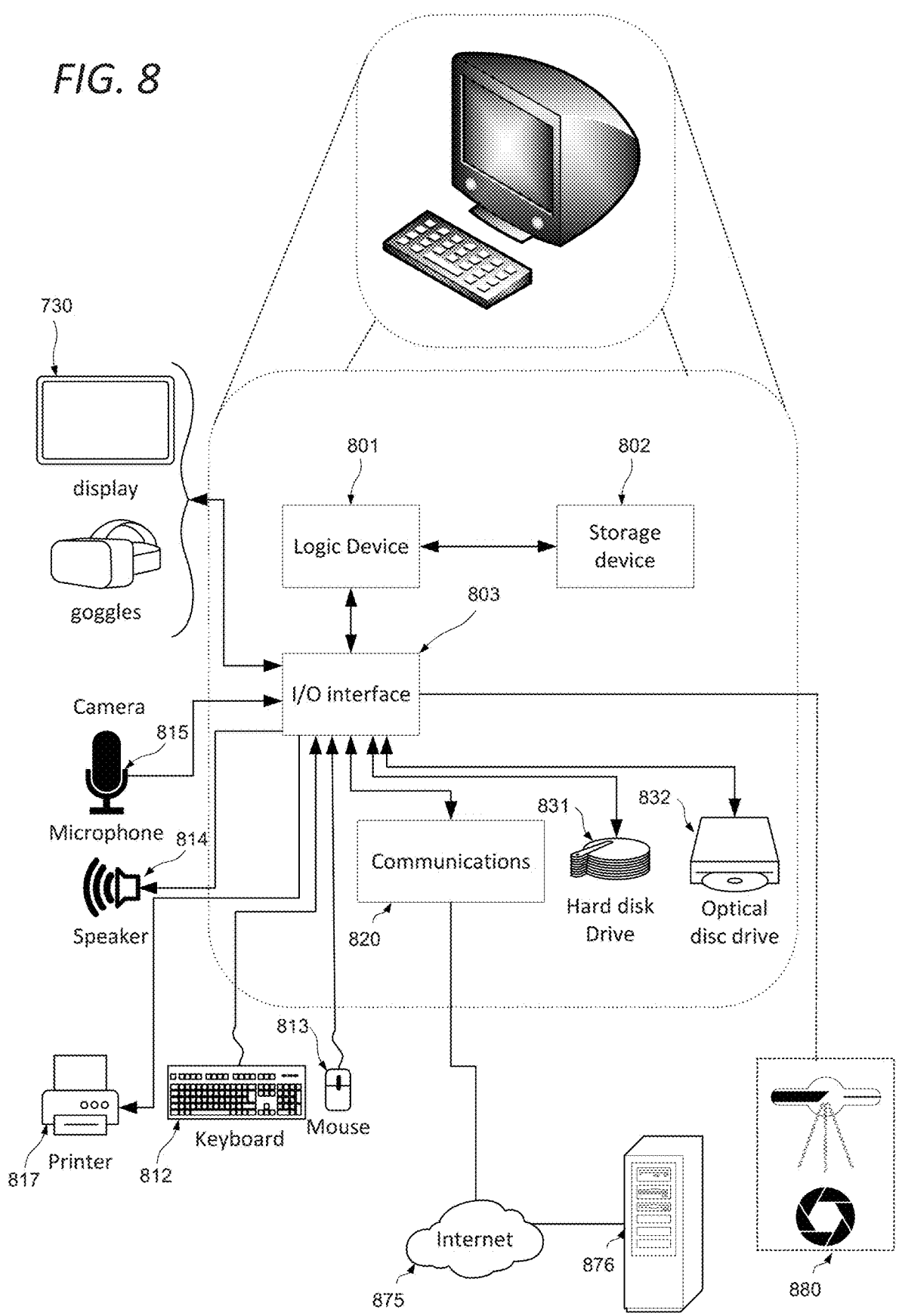
FIG. 8 shows a generic computing system suitable for implementation of embodiments of the invention.

FIG. 8 shows a generic computing system suitable for implementation of embodiments of the invention.

A shown in FIG. 8, a system includes a logic device 801 and a storage device 802. The system may optionally include a display subsystem 730, input/output subsystem 803, communication subsystem 820, and/or other components not shown.

Logic device 801 includes one or more physical devices configured to execute instructions. For example, the logic device 801 may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic device 801 may include one or more processors configured to execute software instructions. Additionally or alternatively, the logic device may include one or more hardware or firmware logic devices configured to execute hardware or firmware instructions. Processors of the logic device may be single-core or multi-core, and the instructions executed thereon may be configured for sequential, parallel, and/or distributed processing. Individual components of the logic device 801 optionally may be distributed among two or more separate devices, which may be remotely located and/or configured for coordinated processing. Aspects of the logic device 801 may be virtualized and executed by remotely accessible, networked computing devices configured in a cloud-computing configuration.

Storage device 802 includes one or more physical devices configured to hold instructions executable by the logic device to implement the methods and processes described herein. When such methods and processes are implemented, the state of storage 802 device may be transformed—e.g., to hold different data.

Storage device 802 may include removable and/or built-in devices. Storage device may be locally or remotely stored (in a cloud for instance). Storage device 802 may comprise one or more types of storage device including optical memory (e.g., CD, DVD, HD-DVD, Blu-Ray Disc, etc.), semiconductor memory (e.g., FLASH, RAM, EPROM, EEPROM, etc.), and/or magnetic memory (e.g., hard-disk drive, floppy-disk drive, tape drive, MRAM, etc.), among others. Storage device may include volatile, non-volatile, dynamic, static, read/write, read-only, random-access, sequential-access, location-addressable, file-addressable, and/or content-addressable devices.

In certain arrangements, the system may comprise an interface 803 adapted to support communications between the logic device 801 and further system components. For example, additional system components may comprise removable and/or built-in extended storage devices. Extended storage devices may comprise one or more types of storage device including optical memory 832 (e.g., CD, DVD, HD-DVD, Blu-Ray Disc, etc.), semiconductor memory (not shown) (e.g., RAM, EPROM, EEPROM, FLASH etc.), and/or magnetic memory 831 (e.g., hard-disk drive, floppy-disk drive, tape drive, MRAM, etc.), among others. Such extended storage device may include volatile, non-volatile, dynamic, static, read/write, read-only, random-access, sequential-access, location-addressable, file-addressable, and/or content-addressable devices.

It will be appreciated that storage device includes one or more physical devices, and excludes propagating signals per se. However, aspects of the instructions described herein alternatively may be propagated by a communication medium (e.g., an electromagnetic signal, an optical signal, etc.), as opposed to being stored on a storage device.

Aspects of logic device 801 and storage device 802 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The term "program" may be used to describe an aspect of computing system implemented to perform a particular function. In some cases, a program may be instantiated via logic device executing machine-readable instructions held by storage device. It will be understood that different modules may be instantiated from the same application, service, code block, object, library, routine, API, function, etc. Likewise, the same program may be instantiated by different applications, services, code blocks, objects, routines, APIs, functions, etc. The term "program" may encompass individual or groups of executable files, data files, libraries, drivers, scripts, database records, etc.

In particular, the system of FIG. 8 may be used to implement embodiments of the invention.

For example a program implementing the steps described with respect to FIG. 3 may be stored in storage device 802 and executed by logic device 801. The three-dimensional environment 720 or data used for the creation of the graphical representation of the objects 721 may be stored in storage 802 or the extended storage devices 832 or 831 and the display 730 used to display the graphical representation. The light guide curve 403 may be input by means of the touchscreen interface, mouse 813, or by other input means.

In some cases, the computing system may comprise or be in communication with a scanner 880 or other three-dimensional imaging system as described above. This communication may be achieved by wired or wireless network, serial bus, Firewire, Thunderbolt™, SCSI or any other communication means as desired. In such cases, a program for the control of the scanner 880 and/or the retrieval of data therefrom may run concurrently on the logic device 801, or these features may be implemented in the same program as implementing the steps described with respect to FIG. 3.

Accordingly the invention may be embodied in the form of a computer program.

Furthermore, when suitably configured and connected, the elements of FIG. 8 may constitute an apparatus adapted to generate a graphical representation of a dataset, and cause a display device to display said representation; this apparatus may further be adapted to receive data from an eye tracking system indicating a point of regard. The apparatus may comprise storage for compiling a record of the point of regard over a duration, and the apparatus may further be adapted to modify the graphical representation to indicate the proportion of the duration for which said point of regard was directed at each point in said representation. This point of regard may then be assimilated to define the light guide curve 403 and/or to define or adjust the position, orientation or field of view of the virtual viewpoint described above.

It will be appreciated that a "service", as used herein, is an application program executable across multiple user sessions. A service may be available to one or more system components, programs, and/or other services. In some implementations, a service may run on one or more server-computing devices.

When included, display subsystem 811 may be used to present a visual representation of data held by a storage device. This visual representation may take the form of a graphical user interface (GUI). As the herein described methods and processes change the data held by the storage device 802, and thus transform the state of the storage device 802, the state of display subsystem 811 may likewise be transformed to visually represent changes in the underlying data. Display subsystem 811 may include one or more display devices utilizing virtually any type of technology for example as discussed above. Such display devices may be combined with logic device and/or storage device in a shared enclosure, or such display devices may be peripheral display devices.

When included, input subsystem may comprise or interface with one or more user-input devices such as a keyboard 812, mouse 813, touch screen 811, or game controller (not shown). In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, colour, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity.

When included, communication subsystem 820 may be configured to communicatively couple computing system with one or more other computing devices. For example, communication module may communicatively couple computing device to remote service hosted for example on a remote server 876 via a network of any size including for example a personal area network, local area network, wide area network, or internet. Communication subsystem may include wired and/or wireless communication devices compatible with one or more different communication protocols. As non-limiting examples, the communication subsystem may be configured for communication via a wireless telephone network 874, or a wired or wireless local- or wide-area network. In some embodiments, the communication subsystem may allow computing system to send and/or receive messages to and/or from other devices via a network such as Internet 875. The communications subsystem may additionally support short range inductive communications with passive or active devices (NFC, RFID etc).

Figure 9:
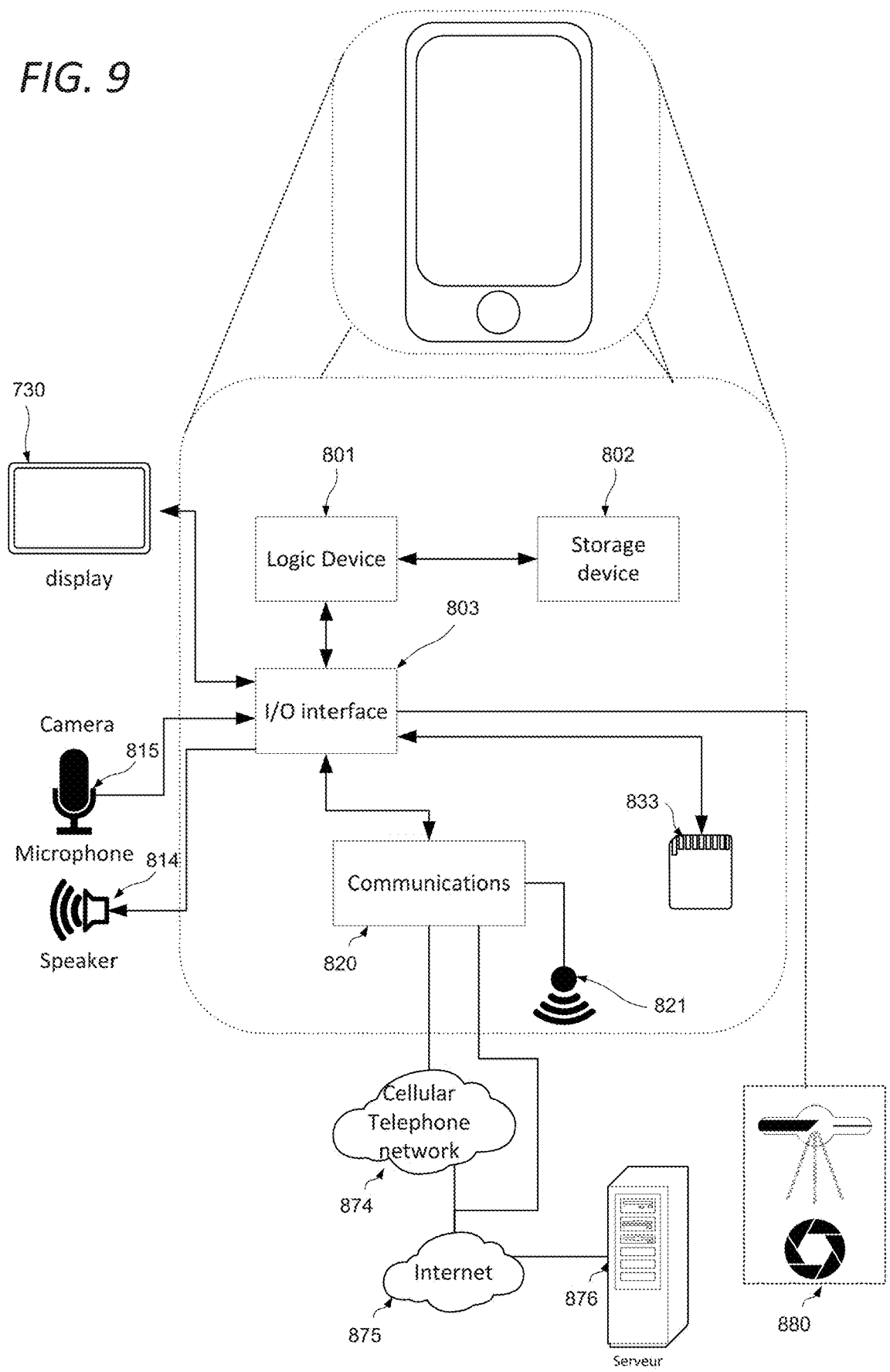
FIG. 9 shows a smartphone device adaptable to constitute an embodiment.
Figure 10:
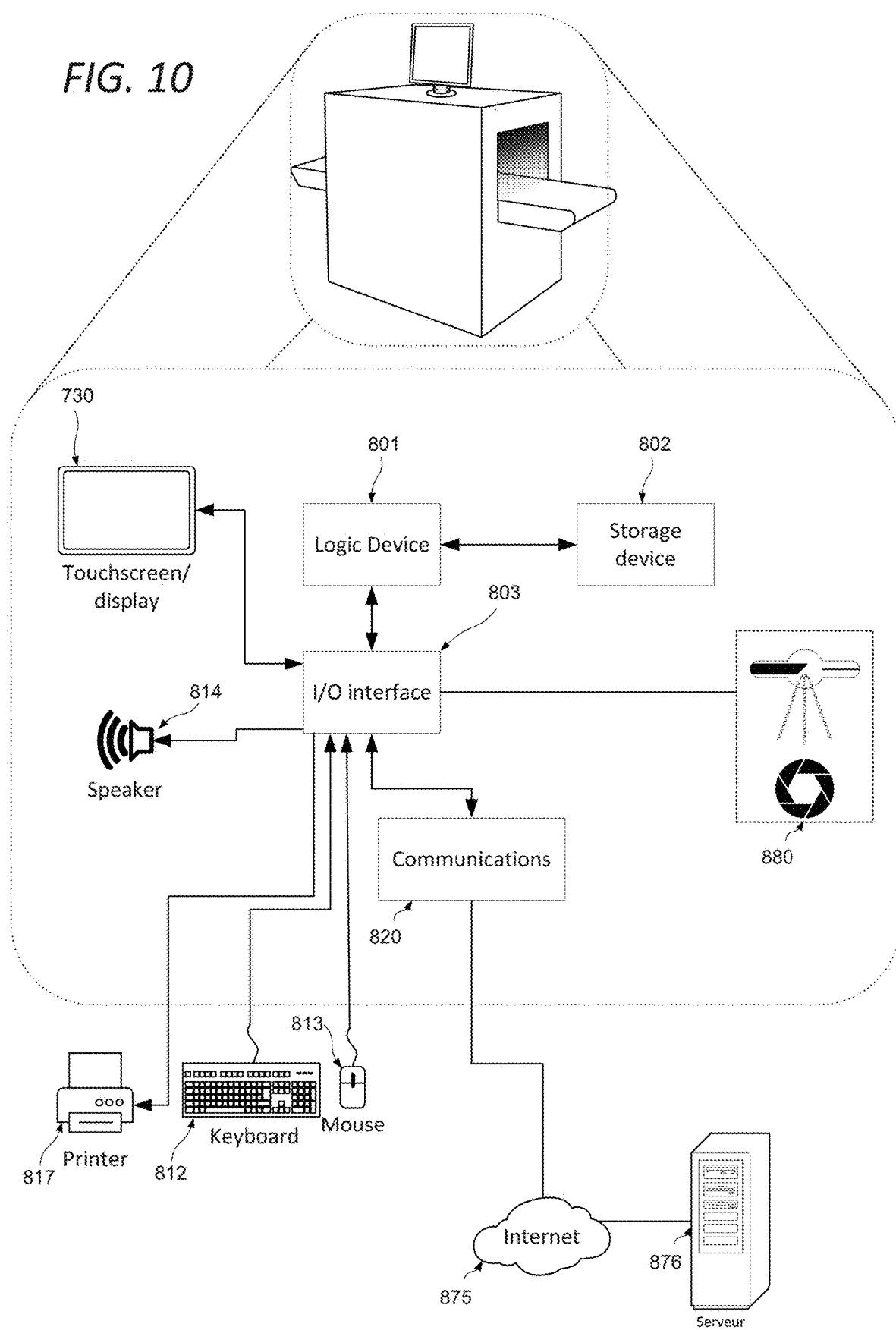
FIG. 10 shows an object scanner system adaptable to constitute an embodiment.
Figure 11:
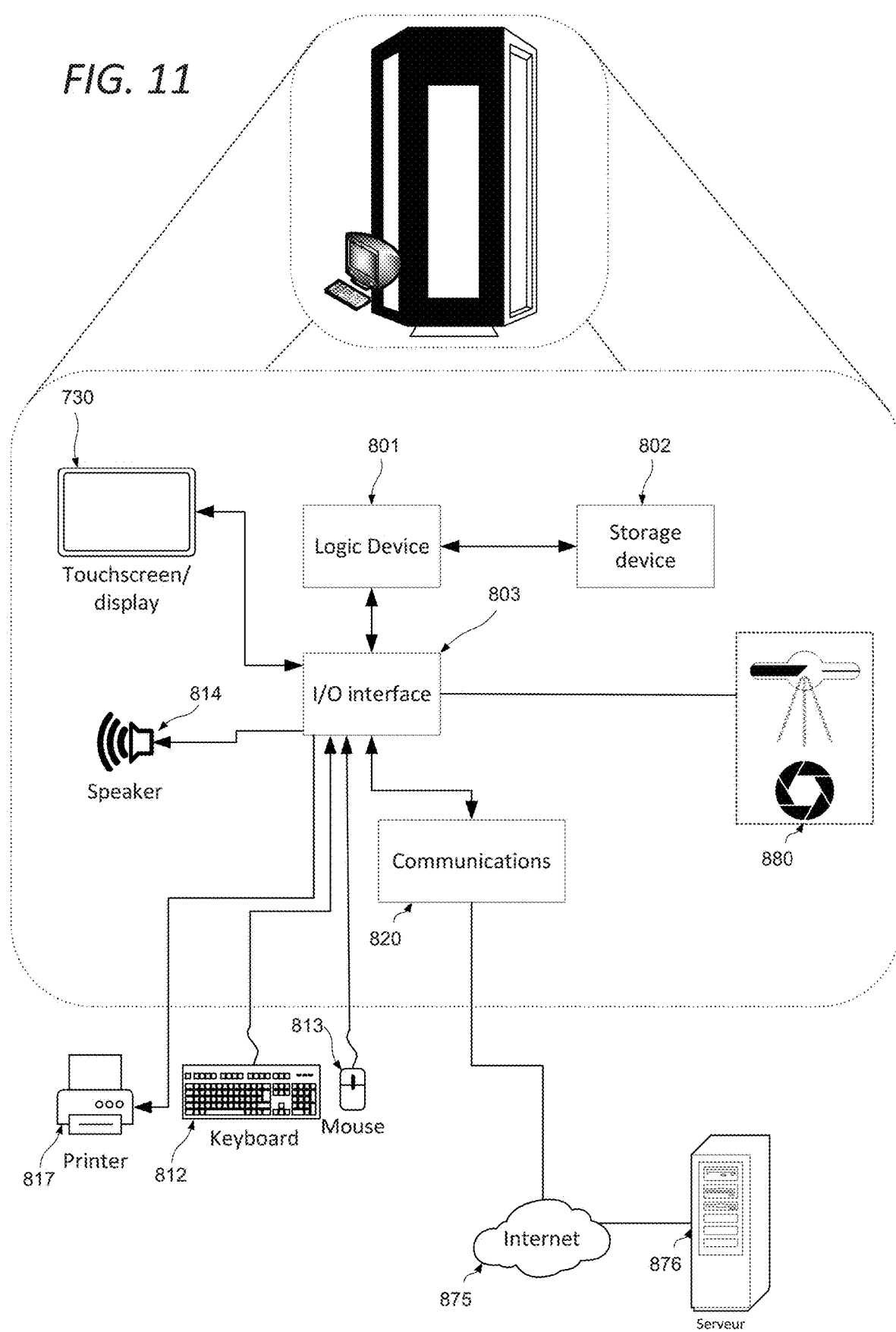
FIG. 11 shows a body scanner system adaptable to constitute an embodiment.

The system of FIG. 8 is intended to reflect a broad range of different types of information handling system. It will be appreciated that many of the subsystems and features described with respect to FIG. 8 are not required for implementation of the invention, but are included to reflect possible systems in accordance with the present invention. It will be appreciated that system architectures vary widely, and the relationship between the different sub-systems of FIG. 8 is merely schematic, and is likely to vary in terms of layout and the distribution of roles in systems. It will be appreciated that, in practice, systems are likely to incorporate different subsets of the various features and subsystems described with respect to FIG. 8. FIGS. 9, 10 and 11 disclose further example devices in accordance with the present invention. Those of ordinary skill in the art will appreciate that systems may be employed in the future which also operate in accordance with the present invention.

FIG. 9 shows a smartphone device adaptable to constitute an embodiment. As shown in FIG. 9, the smartphone device incorporates elements 801, 802, 803, 820, near field communications interface 821, flash memory 833, elements 814, 815, and 730 as described above. It is in communication with the telephone network 874 and a server 876 via the network 875. Alternative communication mechanisms such as a dedicated network or Wi-Fi may also be used. The device may also be in communication with the scanner device 880. The features disclosed in this figure may also be included within a tablet device as well.

FIG. 10 shows an object scanner system adaptable to constitute an embodiment. This example may be representative of a device to be used in airports and the like for scanning baggage and other articles for concealed weapons or contraband. As shown in FIG. 10, the object scanner system comprises elements 801, 802, 803, 820, 814, 817, and 730 as described above. It may be in communication with a server 876 via the network 875. Alternative communication mechanisms such as a dedicated network or Wi-Fi may also be used. The device is also in communication with the scanner hardware 880.

FIG. 11 shows a body scanner system adaptable to constitute an embodiment. This is representative of the devices used in airports, train stations, and the like for scanning individuals for concealed weapons or contraband. As shown in FIG. 11, object scanner system comprises elements 801, 802, 803, 820, 814, 817, and 730 as described above. It may be in communication with a server 876 via the network 875. Alternative communication mechanisms such as a dedicated network or Wi-Fi may also be used. The device is also in communication with the scanner hardware 880.

It will be understood that the configurations and/or approaches described herein are exemplary in nature, and that these specific embodiments or examples are not to be considered in a limiting sense, numerous variations being possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. An apparatus for processing objects including an object of interest and obscuring objects having a spatial relationship in a three-dimensional environment defined by a data set for display, said apparatus comprising:
   a virtual viewpoint selection interface adapted to define a viewpoint in said environment having a specified position, axis of orientation, and field of view therein,
   a light guide curve selection interface adapted to define a non-linear light guide curve which describes a path from said viewpoint to a surface of said object of interest passing around said obscuring objects and converges with said virtual viewpoint,
   a ray tracer adapted to simulate the projection of a plurality of light rays within said environment from said viewpoint, said rays all having an incident angle to said viewpoint within said field of view, and to deviate each ray so as to conform with said light guide curve to a degree proportional to its distance therefrom, and
   an image processor adapted to compile an image composed from the elements of said environment struck by said rays.

2. The apparatus of claim 1 wherein said light guide curve selection interface comprises a human interface device.

3. A method of displaying objects including an object of interest and obscuring objects our having a spatial relationship in a three-dimensional environment defined by a data set, said method comprising:
   defining a non-linear virtual viewpoint in said environment having a specified position, axis of orientation and field of view therein,
   defining a non-linear light guide curve which describes a path from said viewpoint to a surface of said object of interest passing around said obscuring objects and converges with said axis at said virtual viewpoint,
   projecting a plurality of simulated light rays within said environment from said viewpoint, said rays all having an incident angle to said viewpoint within said field of view, and deviating each ray so as to conform with said light guide curve to a degree proportional to its distance therefrom, and
   compiling an image composed from the elements of said environment struck by said rays.

4. The method of claim 3 wherein said light guide curve is defined as one or more polynomial curves.

5. The method of claim 4 wherein said defining a light guide curve comprises defining an initial light guide curve having a knot or control point under user control, and wherein said defining a light guide curve further comprises receiving user input defining a position of said knot or control point and modifying said initial light guide curve to obtain said light guide curve.

6. The method of claim 3 further comprising receiving user input defining said light guide curve.

7. The method of claim 3 wherein said receiving user input defining said light guide curve comprises receiving a manually traced line via a user interface device, said manually traced line representing said light guide curve.

8. The method of claim 7 further comprising translating said manually traced line into one or more polynomial curves in said three-dimensional environment.

9. The method of claim 3 wherein said light guide curve is defined by applying a routing algorithm so as to define a path to a first point in said environment whilst contouring a second point in said environment, where said first point and said second point are designated by user input.

10. The method of claim 3 wherein said guide curve and the proportional relationship according to which any said ray passing within a predetermined distance of said light guide curve at a relative angle within a predetermined range thereto is deviated, together simulate the effect of the optical deformation of a physical lens on said rays.

11. The method of claim 3 wherein said transformation comprises reducing luminous intensity of each ray contributing to said displayed image proportionally to its distance from said light guide curve.

12. The method of claim 3 in which the objects are voxels, polygons, or the objects are defined by intersecting surfaces.

13. The method of claim 3 further comprising receiving an external input determining the orientation, position or field of view of said viewpoint.

14. A non-transitory computer readable storage medium comprising computing instructions for displaying objects including an object of interest and obscuring objects having a spatial relationship in a three-dimensional environment defined by a data set, wherein the computing instructions when executed by one or more processor, configure the one or more processor to:
   define a virtual viewpoint in said environment having a specified position, axis of orientation and field of view therein,
   define a non-linear light guide curve which describes a path from said viewpoint to a surface of said object of interest passing around said obscuring objects and converges with said axis at said virtual viewpoint,
   project a plurality of simulated light rays within said environment from said viewpoint, said rays all having an incident angle to said viewpoint within said field of view, and deviating each ray so as to confirm with said light guide curve to degree proportional to its distance therefrom, and
   compile an image composed from the elements of said environment struck by said rays.

15. The non-transitory computer readable storage medium of claim 14 wherein the one or more processor is further configured to: receive a manually traced line via a user interface device, said manually traced line representing said light guide curve, and translate said manually traced line into one or more polynomial curves in said three-dimensional environment.

* * * * *